US009096486B2

(12) United States Patent
Gildenhuys (10) Patent No.: US 9,096,486 B2
(45) Date of Patent: Aug. 4, 2015

(54) PROCESS FOR POLYMERISING OR OLIGOMERISING A HYDROCARBON

(75) Inventor: Johannes Jochemus Gildenhuys, Johannesburg (ZA)

(73) Assignee: SASOL TECHNOLOGY (PROPRIETARY) LIMITED, Johannesburg (ZA)

(*) Notice: Subject to any disclaimer, the term of this patent is extended or adjusted under 35 U.S.C. 154(b) by 758 days.

(21) Appl. No.: 12/741,834

(22) PCT Filed: Oct. 29, 2008

(86) PCT No.: PCT/IB2008/054457
§ 371 (c)(1),
(2), (4) Date: May 7, 2010

(87) PCT Pub. No.: WO2009/060343
PCT Pub. Date: May 14, 2009

(65) Prior Publication Data
US 2010/0268006 A1    Oct. 21, 2010

(30) Foreign Application Priority Data

Nov. 7, 2007  (ZA) .................................. 2007/09600
Jan. 22, 2008 (ZA) .................................. 2008/00653

(51) Int. Cl.
*C07C 2/02*    (2006.01)
*C07C 2/04*    (2006.01)
(Continued)

(52) U.S. Cl.
CPC ............... *C07C 2/36* (2013.01); *C07C 2531/14* (2013.01); *C07C 2531/24* (2013.01)

(58) Field of Classification Search
USPC ......... 585/312, 313, 314, 315, 324, 326, 502, 585/503, 510, 520, 521, 522, 523
See application file for complete search history.

(56) References Cited

U.S. PATENT DOCUMENTS 5,750,813 A * 5/1998 Hess et al. ...................... 585/12
5,859,159 A * 1/1999 Rossi et al. .................... 526/170
(Continued)

FOREIGN PATENT DOCUMENTS

EP   06 08 707  A1    8/1994
EP    1749807  A1 *  2/2007  ............... C07C 2/30
(Continued)

OTHER PUBLICATIONS

Shah, et al., "Design Parameters Estimations for Bubble Column Reactors" in AIChE Journal, 28(3), 353-379 (1982)—month unknown.*
(Continued)

*Primary Examiner* — In Suk Bullock
*Assistant Examiner* — Youngsul Jeong
(74) *Attorney, Agent, or Firm* — Baker & Hostetler LLP (57) ABSTRACT

A process for polymerizing or oligomerizing a hydrocarbon includes feeding a liquid hydrocarbon reactant and a liquid evaporative cooling medium into a bulk liquid phase which includes polymeric or oligomeric product admixed with a catalyst, and allowing at least a portion of the liquid hydrocarbon reactant and the liquid evaporative cooling medium to vaporize to form bubbles rising through the bulk liquid phase, with the hydrocarbon reactant polymerizing or oligomerizing to form the polymeric or oligomeric product and with the evaporation of both the liquid hydrocarbon reactant and the liquid evaporative cooling medium effecting heat removal from the bulk liquid phase. Gaseous components are withdrawn from a head space, cooled and separated. Condensed hydrocarbon reactant and condensed cooling medium are recycled to the bulk liquid phase.

15 Claims, 6 Drawing Sheets

(51) Int. Cl.
*C07C 2/06* (2006.01)
*C07C 2/08* (2006.01)
*C07C 2/36* (2006.01)

(56) References Cited

U.S. PATENT DOCUMENTS

| | | | |
|---|---|---|---|
| 6,716,936 B1 * | 4/2004 | McGrath et al. | 526/65 |
| 2003/0166456 A1 * | 9/2003 | Wass | 502/102 |
| 2004/0122271 A1 * | 6/2004 | Van Zon et al. | 585/530 |
| 2007/0185362 A1 * | 8/2007 | Lattner et al. | 585/521 |

FOREIGN PATENT DOCUMENTS

| | | |
|---|---|---|
| JP | 10 045638 A | 2/1998 |
| WO | 2004 / 056479 A | 7/2004 |

OTHER PUBLICATIONS

Lide, CRC Handbook of Chemistry and Physics, 91st edition, 2011 Internet Version, D. R. Lide, editor—month unknown.*

* cited by examiner

PROCESS FOR POLYMERISING OR OLIGOMERISING A HYDROCARBON

CROSS-REFERENCE TO RELATED APPLICATIONS

This application is a National Stage of International Patent Application No. PCT/IB2008/054457, filed on Oct. 29, 2008, which claims priority to foreign Patent Application No. ZA 2007/09600, filed on Nov. 7, 2007, and foreign Patent Application No. ZA 2007/00653, filed on Jan. 22, 2008, the disclosures of which are incorporated herein by reference in their entirety.

FIELD OF THE INVENTION

THIS INVENTION relates to a process for polymerising or oligomerising a hydrocarbon.

SUMMARY OF THE INVENTION

According to the invention, there is provided a process for polymerising or oligomerising a hydrocarbon, the process including
feeding a liquid hydrocarbon reactant and a liquid evaporative cooling medium into a bulk liquid phase which includes polymeric or oligomeric product admixed with a catalyst;
allowing at least a portion of the liquid hydrocarbon reactant and the liquid evaporative cooling medium to vapourise to form bubbles rising through the bulk liquid phase, with the hydrocarbon reactant polymerising or oligomerising to form the polymeric or oligomeric product and with the evaporation of both the liquid hydrocarbon reactant and the liquid evaporative cooling medium effecting heat removal from the bulk liquid phase;
allowing gaseous components comprising any unreacted vapourised hydrocarbon reactant and vapourised cooling medium and any gaseous product that may have formed to disengage from the bulk liquid phase into a head space above the bulk liquid phase;
withdrawing the gaseous components from the head space;
cooling the gaseous components withdrawn from the head space, forming condensed hydrocarbon reactant and condensed cooling medium and gaseous product;
separating the condensed hydrocarbon reactant and condensed cooling medium from the gaseous product and withdrawing the gaseous product;
recycling the condensed hydrocarbon reactant and the condensed cooling medium to the bulk liquid phase; and
withdrawing liquid phase to maintain the bulk liquid phase at a desired level.

The bulk liquid phase may be contained in a bubbling column reactor, with the rising bubbles creating turbulence in the bulk liquid phase, thereby also mixing the bulk liquid phase. When the bulk liquid phase is contained in a bubbling column reactor, the liquid or condensed hydrocarbon reactant and the condensed cooling medium are typically fed at or near a bottom of the bubbling column reactor.

Instead, the bulk liquid phase may be contained in a continuously stirred tank reactor.

The bulk liquid phase may include an inert solvent, e.g. to act as a diluent thereby limiting incorporation of desirable oligomeric product in lower value heavier by-products. Any inert solvent that does not react with components of the bulk liquid phase, and which does not crack in the temperature range 25 to 300° C. can be used. These inert solvents may include saturated aliphatics, unsaturated aliphatics, aromatic hydrocarbons and halogenated hydrocarbons. Typical solvents include, but are not limited to, benzene, toluene, xylene, cumene, heptane, methylcyclohexane, methylcyclopentane, cyclohexane, Isopar C, Isopar E, 2,2,4-trimethylpentane, Norpar, chlorobenzene, 1,2-dichlorobenzene, ionic liquids and the like.

The gaseous product typically includes uncondensed unreacted hydrocarbon reactant and possibly uncondensed cooling medium. The process may include treating the gaseous product to recover uncondensed unreacted hydrocarbon reactant and/or uncondensed cooling medium from the gaseous product. This treatment may include at least one distillation stage, recovering the hydrocarbon reactant and/or the cooling medium for recycle to the bulk liquid phase.

The process may include treating the withdrawn liquid phase to separate polymeric or oligomeric product from solvent. The treatment of the liquid phase may include subjecting the liquid phase to at least one distillation stage to obtain a solvent stream. The solvent stream may be recycled to the bulk liquid phase.

The polymerisation or oligomerisation reaction or reactions in the bulk liquid phase are exothermic, requiring cooling of the bulk liquid phase. In the process of the invention, this heat removal is at least predominantly effected by means of the latent heat required for evaporation of the liquid evaporative cooling medium and the liquid hydrocarbon reactant. Sufficient liquid evaporative cooling medium and liquid hydrocarbon reactant may be fed and recycled to the bulk liquid phase to balance any reaction exotherm, thereby approaching isothermal behaviour, i.e. maintaining a steady temperature in the bulk liquid phase. This feature of the invention is important, as the absence of a heat exchanger in direct contact with the bulk liquid phase reduces the surface area that may be susceptible to fouling, which is often a problem with polymerisation or oligomerisation processes. Furthermore, in one embodiment of the invention, the vigorous mixing caused by the vapourisation of liquid droplets of the hydrocarbon reactant and the evaporative cooling medium as they enter the bulk liquid phase to form rising gas bubbles (e.g. in the case of a bubbling column) obviates the need for a stirrer or agitator, which may also be susceptible to fouling.

The liquid hydrocarbon reactant may be an olefinic feedstock, i.e. comprising one or more olefinic monomers. Preferably, the olefinic feedstock comprises predominantly α-olefins, e.g. ethylene.

The process may thus be an oligomerisation process. In one embodiment of the invention, the process is predominantly a trimerisation process. In another embodiment of the invention, the process is predominantly a tetramerisation process.

In a further embodiment, the process is predominantly both a trimerisation process and a tetramerisation process.

The liquid hydrocarbon reactant may thus be liquid ethylene. The liquid hydrocarbon reactant being fed to the bulk liquid phase is preferably sub-cooled. The degree of sub-cooling is preferably sufficient to prevent premature flashing of the liquid hydrocarbon in a feed line and/or nozzle used to feed the liquid hydrocarbon to the bulk liquid phase.

When the liquid hydrocarbon reactant is liquid ethylene, the bulk liquid phase may be at an operating pressure of at least about 1 bar(a), more preferably at least about 10 bar(a), most preferably at least about 30 bar(a), e.g. between about 45 bar(a) and about 50 bar(a). The temperature of the bulk liquid phase may be from about 30 to about 100° C., preferably from about 40 to about 80° C., e.g. between about 50 and about 70° C.

The evaporative cooling medium is typically a hydrocarbon which acts as an inert in the oligomerising or polymerising reactions, and which acts to increase the bubble point temperature of an admixture or condensate obtained by condensing the vapourised hydrocarbon reactant and the vapourised evaporative cooling medium withdrawn from the head space above the bulk liquid phase, disregarding other lighter components which may be present in the gaseous components withdrawn from the head space above the bulk liquid phase. Preferably, the evaporative cooling medium, and the concentration of the evaporative cooling medium in the bulk liquid phase of the bubbling column, are selected such that the bubble point temperature of the gaseous components withdrawn from the head space above the bulk liquid phase, at the pressure at which the gaseous components are cooled for condensation purposes, is preferably at least 30° C., and more preferably at least 40° C. This bubble point temperature should however be lower than the temperature of the bulk liquid phase, providing for an adequate temperature driving force to enable vapourisation of at least a portion of the liquid hydrocarbon reactant and the liquid cooling medium fed into the bulk liquid phase. Advantageously, with a bubble point temperature in the order of, say 30 to 55° C., it is possible to cool the gaseous components withdrawn from the head space above the bulk liquid phase with plant cooling water, obviating the need for refrigerated water as a cooling utility for purposes of cooling and condensing a major portion of the gaseous components withdrawn from the head space above the bulk liquid phase. As will be appreciated, this provides a significant economic benefit to the process of the invention.

The evaporative cooling medium may be any inert component or mixture of components that does not react with components of the bulk liquid phase, preferably having a normal boiling point within the range of −20 to −60° C., and may include, but is not limited to, propane, cyclopropane, chlorodifluoromethane, difluoromethane, 1,1,1-trifluoroethane, pentafluoroethane, octafluoropropane, 1,1,1,2-tetrafluoroethane, trifluorobromomethane, chlorotrifluoroethylene, chloropentafluoroethane, ethyl-fluoride, 1,1,1-trifluoroethane, chloropentafluoroethane, and mixtures of two or more of these.

The solvent and the evaporative cooling medium may in some embodiments of the invention be the same. In other words, the evaporative cooling medium may also act as an inert solvent or diluent to limit incorporation of desirable polymeric or oligomeric product in lower value or heavier by-products, with no other solvent being added to the bulk liquid phase.

The bulk liquid phase may form part of a first oligomerisation stage. The process may include feeding the withdrawn liquid phase from the first oligomerisation stage to a second oligomerisation stage comprising bulk liquid phase, and feeding said liquid hydrocarbon reactant also into the bulk liquid phase of the second oligomerisation stage, to form further polymeric or oligomeric product. In other words, the process may use at least two oligomerisation stages in series for the bulk liquid phase, with fresh liquid hydrocarbon reactant being fed into the bulk liquid phase of each oligomerisation stage (i.e. the oligomerisation stages are in parallel for the liquid hydrocarbon reactant), and preferably with the withdrawn gaseous components from the head spaces above the bulk liquid phase of each oligomerisation stage being combined and with the condensed hydrocarbon reactant and the condensed cooling medium being recycled, e.g. in parallel, to the bulk liquid phase of both of the oligomerisation stages.

The process may include treating the withdrawn liquid phase to separate unreacted hydrocarbon reactant and/or cooling medium from the polymeric or oligomeric product. This treatment may include subjecting the liquid phase to at least one distillation stage and withdrawing the unreacted hydrocarbon reactant and/or cooling medium as an overhead stream from the distillation stage. The withdrawn unreacted hydrocarbon reactant and/or cooling medium may be recycled to the bulk liquid phase. It will be appreciated that for embodiments of the invention where the solvent and the evaporative cooling medium are the same, a single treatment stage may be employed to separate unreacted hydrocarbon reactant and/or cooling medium/solvent from polymeric or oligomeric product. The separated unreacted hydrocarbon reactant and the separated cooling medium/solvent may be returned as a single stream to the bulk liquid phase. In such an embodiment of the invention, the need for an additional treatment stage for recovery of a solvent different to the evaporative cooling medium is thus obviated.

The use of a highly polar evaporative cooling medium is preferential to the use of a less or non-polar evaporative cooling medium, so as to provide adequate solubility of the catalyst in the portion of the evaporative cooling medium forming part of and acting as diluent in the bulk liquid phase, thereby possibly obviating the need for an additional inert solvent as hereinbefore described.

In one embodiment of the invention, the evaporative cooling medium is propane. In another embodiment of the invention, the evaporative cooling medium is chlorodifluoromethane. Preferably, the mass fraction of propane in ethylene is between about 0.3 and about 0.7, most preferably between about 0.4 and about 0.6.

The trimerisation of ethylene to 1-hexene is a significant commercial operation. In addition to its use as a specific chemical, 1-hexene is extensively used in polymerisation processes either as a monomer or co-monomer. The trimeric products derived from longer chain olefins can be used as synthetic lubricants (e.g. as polyalphaolefins) and in applications such as components of drilling muds and as a feedstock to prepare detergents and plasticizers.

In one embodiment of the invention, the catalyst is a dissolved transition metal compound catalyst, e.g. a chromium catalyst, with a heteroatomic or homoatomic, ligand, typically used with an activator. A number of dissolved transition metal compound catalysts have been developed for use to trimerise or tetramerise olefins, e.g. as disclosed in U.S. Pat. No. 4,668,838; EP 0668105; U.S. Pat. No. 5,750,817; U.S. Pat. No. 6,031,145; U.S. Pat. No. 5,811,618; WO 03/053890; WO 2004/056478; WO 2004/056477; WO 2004/056479; WO 2004/056480; WO 2005/123633 and WO 2007/007272, all of which are incorporated herein by reference. The catalyst may instead be a nickel catalyst comprising a chelating ligand, e.g. 2-diphenyl phosphine benzoic acid, typically used with a catalyst activator such as sodium tetraphenylborate. Also possible is the use of trialkylaluminium catalysts.

Some of these catalysts are selective for $C_6$ and $C_8$ oligomeric products, e.g. 1-hexene and 1-octene, and the Applicant believes that such catalysts will be particularly advantageous for use with the process of the invention as the selective production of 1-hexene and 1-octene is commercially important.

Suitable activators include organoaluminium compounds, boron compounds, organic salts, such as methyl lithium and methyl magnesium bromide, inorganic acids and salts, such as tetrafluoroboric acid etherate, silver tetrafluoroborate, sodium hexafluoroantimonate, aluminate activators e.g. trityl perfluoro-tributyl aluminate, and the like.

Organoaluminium compounds which act as suitable activators include alkylaluminium compounds such as trialkylaluminium and aluminoxanes.

Aluminoxane activators are well known in the art and can be prepared by the controlled addition of water to an alkylaluminium compound, such as trimethylaluminium. In such process the alkylaluminium compounds are only partially hydrolysed to prevent or at least to reduce the formation of aluminium hydroxide during the preparation of aluminoxanes. Commercially available aluminoxanes consequently include unreacted alkylaluminium. The result is that commercially available aluminoxanes are usually mixtures of an aluminoxane and an alkylaluminium.

In this specification the term "aluminoxanes" is used to denote a compound represented by the general formulae $(R^a—Al—O)_n$ and $R^b(R^c—Al—O)_n—AlR^d{}_2$ wherein $R^a$, $R^b$, $R^c$, and $R^d$ are independently a $C_1$-$C_{30}$ alkyl or halo-alkyl radical, for example methyl, ethyl, propyl, butyl, 2-methylpropyl, pentyl, isopentyl, neopentyl, cyclopentyl, hexyl, isohexyl, cyclohexyl, heptyl, octyl, iso-octyl, 2-ethyl-hexyl, decyl, 2-phenyl-propyl, 2-(4-fluorophenyl)-propyl, 2,3-dimethyl-butyl, 2,4,4-trimethyl-pentyl and dodecyl; and n has the value of 2 to 50. Preferably n is at least 4.

In one embodiment of the invention the oligomerisation catalyst includes a combination of
i) a source of Cr; and
ii) a ligating compound of the formula wherein:
$X^1$ and $X^2$ are independently selected from the group consisting of N, P, As, Sb, Bi, O, S and Se;
Y is a linking group between $X^1$ and $X^2$;
m and n are independently 0, 1 or a larger integer; and
$R^1$ and $R^2$ are independently hydrogen, a hydrocarbyl group or a heterohydrocarbyl group, and $R^1$ being the same or different when m>1, and $R^2$ being the same or different when n>1.

In this specification a heterohydrocarbyl group is a hydrocarbyl group which includes at least one heteroatom (that is not being H or C), and which organic compound binds with one or more other moieties through one or more carbon atoms of the organic compound and/or one or more heteroatoms of the organic compound. Organoheteryl groups and organyl groups (which include at least one heteroatom) are examples of heterohydrocarbyl groups.

Preferably the ligating compound is of the formula with $R^3$ to $R^7$ as defined above.

Preferably each of $R^3$ to $R^6$ is an alkyl (preferably methyl, ethyl or isopropyl) or aromatic (preferably phenyl or substituted phenyl).

Non limiting examples of the ligating compound are
(phenyl)$_2$PN(propyl)P(phenyl)$_2$;
(phenyl)$_2$PN(cyclopentyl)P(phenyl)$_2$;
(phenyl)$_2$PN(isopropyl)P(phenyl)$_2$;
(phenyl)$_2$PN((4-t-butyl)-phenyl)P(phenyl)$_2$;
(2-naphthyl)$_2$PN(methyl)P(phenyl)$_2$;
(2-methylphenyl)(phenyl)PN(isopropyl)P(2-methylphenyl)(phenyl);
(ethyl)(phenyl)P-1,2-benzene-P(ethyl)(phenyl);
(4-methoxyphenyl)$_2$PN(isopropyl)P(phenyl)$_2$;
(2-methoxyphenyl)$_2$P-1,2-benzene-P(2-methoxyphenyl)$_2$
(phenyl)$_2$PN(1,2-dimethylpropyl)P(phenyl)$_2$;
(phenyl)$_2$PN(cyclopentyl)P(phenyl)$_2$; (phenyl)$_2$PN(cyclohexyl)P(phenyl)$_2$;
(phenyl)$_2$PN(1-adamantyl)P(phenyl)$_2$;
(phenyl)$_2$PN(2-adamantyl)P(phenyl)$_2$;
(phenyl)$_2$PN(S-Chipros)P(phenyl)$_2$;
(phenyl)$_2$P—N(methyl)-N-(isopropyl)P(phenyl)$_2$;
(phenyl)$_2$P—N(methyl)-N-(ethyl)P(phenyl)$_2$;
(phenyl)$_2$P—N(ethyl)-N-(ethyl)P(phenyl)$_2$;
(2-isopropylphenyl)$_2$PN(methyl)P(2-isopropylphenyl)$_2$ and
(2-methoxyphenyl)$_2$PN(methyl)P(2-methoxyphenyl)$_2$.

BRIEF DESCRIPTION OF THE DRAWINGS

The invention will now be described, by way of example, with reference to the accompanying drawings in which.

DETAILED DESCRIPTION

Figure 1:
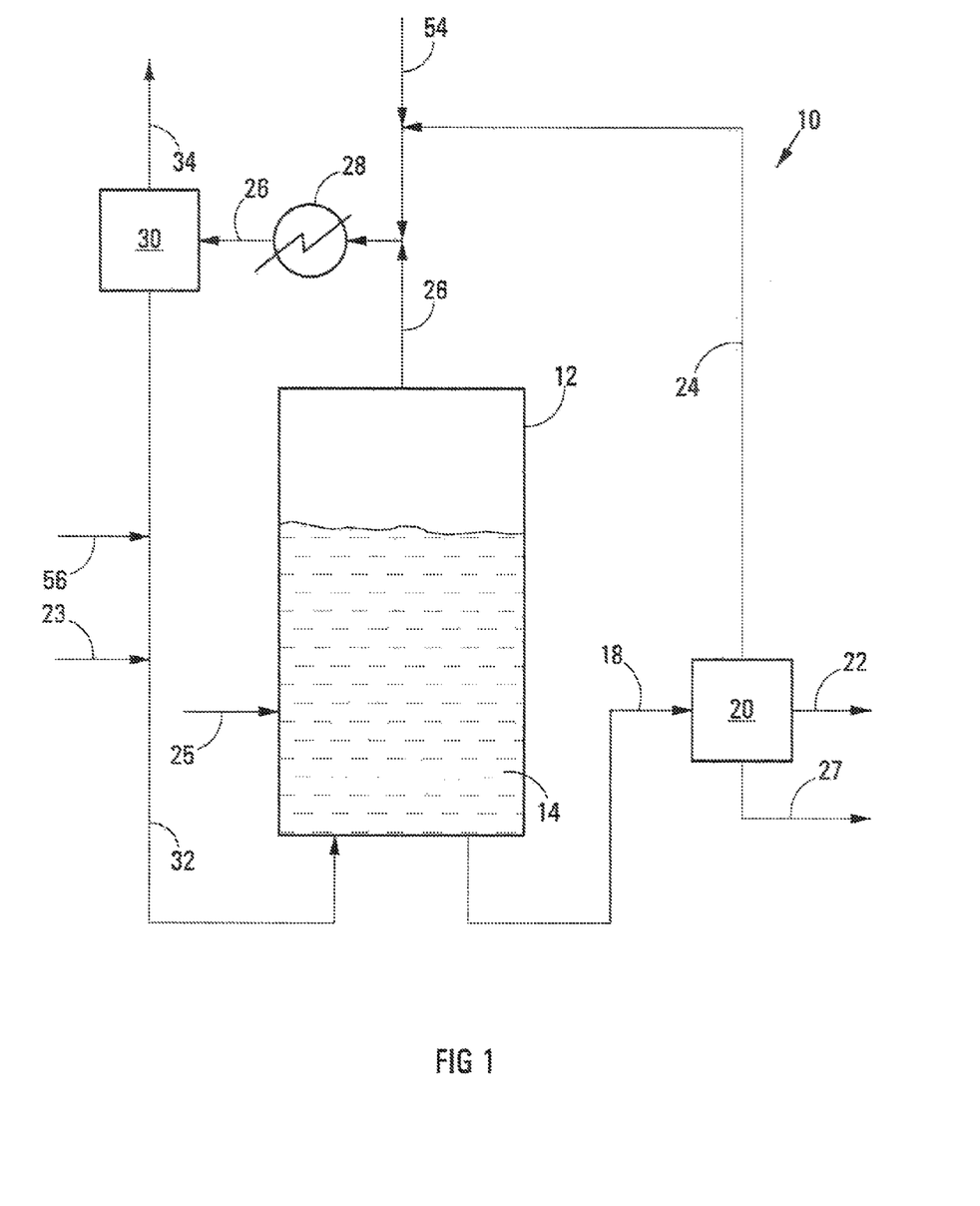
FIG. 1 shows one embodiment of a process in accordance with the invention for polymerising or oligomerising a hydrocarbon.

Referring to FIG. 1 of the drawings, reference numeral 10 generally indicates a process in accordance with the invention for polymerising or oligomerising a hydrocarbon. The process 10 as shown in the drawing is in particular for the tetramerisation, and to a lesser extent trimerisation, of ethylene but it can also be used for the polymerisation or oligomerisation of other olefinic feedstocks.

The process 10 includes a reactor 12 containing a bulk liquid phase 14 in the form of a bubbling column. The reactor 12 is thus a bubbling column reactor. Recycled liquid ethylene as hydrocarbon reactant and recycled liquid propane as evaporative cooling medium enter the bottom of the reactor 12 from a line 32 so that the liquid ethylene and liquid propane in use enter the bottom of the bubbling column of bulk liquid phase 14. A solvent line 23 joins the line 32. A catalyst line 25 leads into the reactor 12.

A liquid phase withdrawal line 18, preferably with a bottom withdrawal point leaves from the reactor 12 to a treatment stage 20, with an oligomeric product line 22, a recovered ethylene and propane line 24, and a solids line 27 leaving the treatment stage 20. A gaseous components line 26 leaves from a top of the reactor 12 to a partial condenser 28 and leads from the partial condenser 28 to a separator 30. The recovered ethylene and propane line 24 from the treatment stage 20 joins the gaseous components line 26 leading into the partial condenser 28. A propane make-up line 56 joins the line 32 and a fresh gaseous ethylene line 54 joins the recovered ethylene and propane line 24.

The line 32 is a liquid ethylene and propane recycle line which leads from the separator 30 to the reactor 12, with a gaseous product line 34 also leading from the separator 30.

In order to trimerise and tetramerise ethylene to produce 1-hexene and 1-octene, liquid ethylene (predominantly recycled but with a small portion of fresh ethylene) is fed by means of the line 32 into the bottom of the bulk liquid phase 14 inside the reactor 12. The reactor 12 is operated typically at a pressure of between about 45 bar(a) and 50 bar(a), with the bulk liquid phase 14 being at a temperature below its boiling point at the operating pressure of the reactor 12. Typically, this temperature is about 60° C.

The bulk liquid phase 14 of the bubbling column includes an admixture of ethylene, oligomeric products, a solvent which includes a dissolved catalyst system, propane as evaporative cooling medium, and small amounts of solids formed by undesirable side reactions. Typical mass concentrations dissolved in the liquid phase are about 20-25 mass % ethylene, 5-15 mass % oligomeric product, 5-10 mass % solvent and 50-70 mass % propane as evaporative cooling medium. The mass fraction of propane in ethylene in the feed line 32 is 0.5. Fast rising bubbles of vapourised ethylene and propane pass upwardly through the bubbling column of bulk liquid phase 14. In the embodiment of the invention shown in FIG. 1, the solvent is a $C_8$ paraffin (Isopar-C), with the catalyst system comprising Cr (chromium), (phenyl)$_2$PN(isopropyl)P(phenyl)$_2$ ligand and methyl aluminoxane as activator.

The reactor 12 with the particular catalyst system primarily produces 1-hexene and 1-octene from ethylene. In other words, the reactor 12 primarily trimerises and tetramerises the ethylene. The oligomerisation reactions taking place inside the reactor 12 are exothermic. The heat of reaction is sufficient to provide the energy required to heat the incoming liquid ethylene and liquid propane feed to 60° C. and to maintain the bulk liquid phase at a temperature below its boiling temperature but above the boiling temperature of the liquid ethylene and liquid propane mixture thereby to vapourise liquid ethylene and liquid propane in the bulk liquid phase 14, ensuring that the bulk liquid phase 14 is in the form of a bubbling column. The vapourisation of the liquid ethylene and liquid propane and hence the formation of fast rising gas bubbles creates vigorous mixing inside the bulk liquid phase 14, turning the bulk liquid phase 14 into a bubbling column. This is important and advantageous in the embodiment of the invention shown in FIG. 1, as it may allow the reactor 12 to operate without a stirrer or agitator, which, if present, may be susceptible to fouling. Temperature control of the reactor 12 is effected by means of flashing of liquid ethylene and liquid propane so there is no need for a heat exchanger in direct contact with the bulk liquid phase 14 to remove heat from the bulk liquid phase 14 (i.e. direct-contact cooling or so-called "hot cooling" is employed, using the inert liquid propane as evaporative cooling medium in combination with evaporation of liquid ethylene reactant).

In general, ethylene oligomerisation processes form small quantities of solids and process designs are required that can handle this material. One solution is to design a catalyst or catalyst system which can be used at a temperature high enough to have the fouling polymer solids in solution, thereby to prevent fouling. Alternatively, if the operating temperature of the process is too low so that precipitation will occur, a conventional approach is to use an external heat exchanger to prevent contact of heat exchange surfaces and process fluids with the fouling polymers. With the process of the invention as illustrated in FIG. 1, a liquid hydrocarbon feed that has a boiling temperature lower than the bulk temperature of the liquid phase of the bubbling column at the reaction pressure is used so that, on contact with the bulk liquid phase, the liquid hydrocarbon will vapourise rapidly releasing bubbles that induce turbulence and generate sufficient mixing in the reactor. This can eliminate the requirement for an agitator and hence agitator fouling as a reason for plant shutdown, extending run times and increasing plant availability and hence reducing the need for increased plant size to meet capacity requirements. Given that phase change results in a large change in density for a given mass of liquid hydrocarbon fed into the reactor, a significant amount of work can be carried out on the bulk liquid phase bubbling column by vapourising the liquid hydrocarbon stream in the bulk liquid phase, while maintaining an isothermal reaction environment. Given that a fouling process such as a tetramerisation process requires periodic cleaning, the fact that an agitator may not be needed to maintain good mixing under reaction conditions allows a more tailored design to be implemented to allow for optimisation of a reactor cleaning step.

The liquid phase is withdrawn through the liquid phase withdrawal line 18 to maintain the bulk liquid phase 14 at a desired level within the reactor 12. A catalyst kill reagent, e.g. an alcohol such as ethanol, may be introduced to the withdrawn liquid product stream to prevent further reaction. The liquid phase is treated in the treatment stage 20, providing an unreacted or recovered gaseous ethylene and propane stream which is withdrawn along line 24 and eventually returned in liquid form to the reactor 12 (together with any make-up liquid propane fed by means of the make-up propane line 56 and fresh ethylene fed by means of the gaseous ethylene line 54), via the partial condenser 28, separator 30 and the recycle line 32.

An oligomeric product is withdrawn from the treatment stage 20 by means of the oligomeric product line 22, and small amounts of solids are withdrawn through the solids line 27. In FIG. 1, the treatment stage 20 is represented by a single block. In practice, the separation of unreacted ethylene and liquid propane and polymer solids that may have formed from the liquid phase requires a complex series of separation steps typically including at least one distillation or flash stage and possibly one compression stage. As the recovery of unreacted ethylene and propane and separation of solids from the liquid product is however peripheral to the present invention, this will not be discussed in any more detail.

The process 10 will typically also include recovering the solvent from the oligomeric product. The solvent is then returned to the reactor 12. Recovery is typically effected using a distillation column, but the details of this recovery are also not required for an understanding of the present invention and will not be discussed in any detail.

Gaseous components, including unreacted vapourised ethylene and vapourised propane and any gaseous product that may have formed in the reactor 12, are collected in a headspace above the bulk liquid phase 14 and withdrawn through the gaseous components line 26. The gaseous components may also include light impurities, such as hydrogen, methane which may have entered the process 10 with the liquid ethylene feed and ethane formed in the reactor 12 as a by-product. Methane may also be liberated in a catalyst deactivation reaction, particularly when the catalyst includes an aluminium specie, as a result of the reaction of an alcohol with the aluminium specie. The partial pressure of light impurities, e.g. methane and ethane, in the reactor 12 should be minimised as far as practically possible, to increase the ethylene partial pressure thereby increasing the ethylene concentration in the bulk liquid phase 14, and hence increasing the productivity of the reactor 12.

Figure 5:
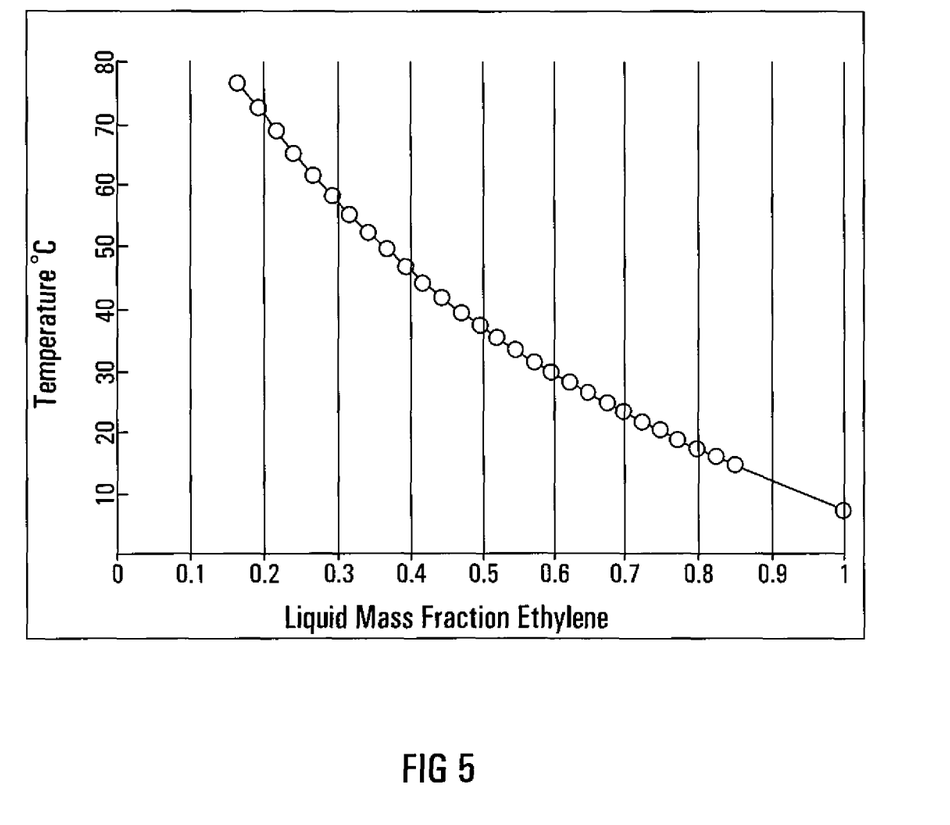
FIG. 5 shows a graph of the bubble point temperature of a binary ethylene/propane system as a function of ethylene concentration, at a pressure of 48 bar(a)
Figure 6:
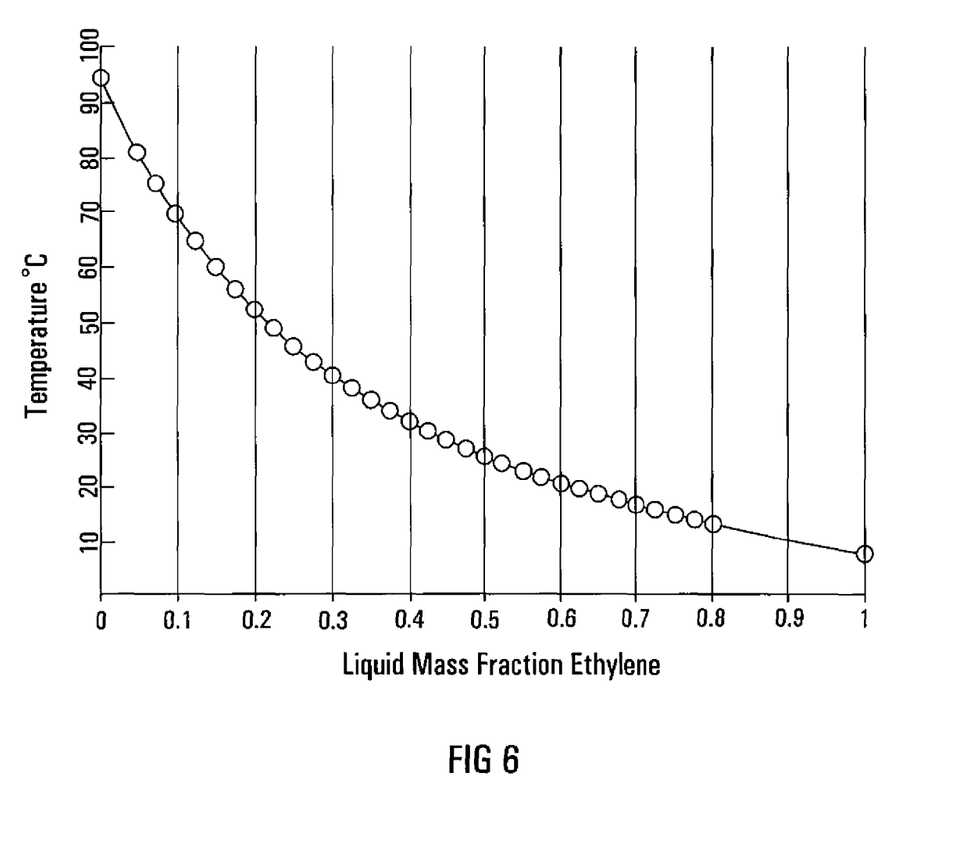
FIG. 6 shows a graph of the bubble point temperature of a binary ethylene/chlorodifluoromethane system as a function of ethylene concentration, at a pressure of 48 bar(a).

In the partial condenser 28, the gaseous components withdrawn along the gaseous components line 26 are cooled, forming a mixture of condensed ethylene and propane which is knocked out in the separator 30 and returned to the reactor 12 by means of the liquid ethylene recycle line 32. Advantageously, by selecting appropriate operating conditions and an appropriate propane concentration in the bulk liquid phase 14, it is possible to raise the bubble point temperature of the ethylene and propane mixture sufficiently high, e.g. preferentially above 30° C., more preferentially above 40° C., so that plant cooling water can be used in the partial condenser 28 to condense the bulk of the vapour introduced into the condensor, i.e. at least 99 molar % of vapour introduced into the condensor, in stead of refrigerated water which would be the case if propane was not present in a sufficiently high concentration. Thus, as illustrated by FIG. 5, a propane concentration higher than about 45% by mass, e.g. about 55% by mass, in the vapour entering the partial condenser 28 will allow plant cooling water to be used as cooling utility in the partial condenser 28. The lower limit of the propane concentration will naturally be affected by the concentration of other inert lights, such as methane and ethane, in the gaseous stream entering the partial condenser 28. In stead of propane, other inert hydrocarbons, such as chlorodifluoromethane can be used as evaporative cooling medium. As can be seen from FIG. 6, a chlorodifluoromethane mass concentration higher than about 60%, e.g. about 70% will allow plant cooling water to be used as cooling utility in the partial condenser 28.

Uncondensed gaseous components, i.e. gaseous product and some gaseous inerts, are withdrawn from the separator 30 by means of the gaseous product line 34. Although not shown in FIG. 1 of the drawings, the process 10 may include treating the gaseous product withdrawn by means of the gaseous product line 34 to recover uncondensed unreacted ethylene and possibly uncondensed propane from the gaseous product. Typically, such a treatment will include at least one distillation stage operating at a lower pressure and a lower temperature than the reactor 12, producing ethylene and propane which can be recycled to the reactor 12.

Naturally, the process 10 may include treating the oligomeric product from the treatment stage 20 to separate desired components, such as 1-hexene, 1-octene, a cyclic $C_6$ product and a $C_{10}$+ product and solvent. Such separation will typically take place in distillation columns.

Figure 2:
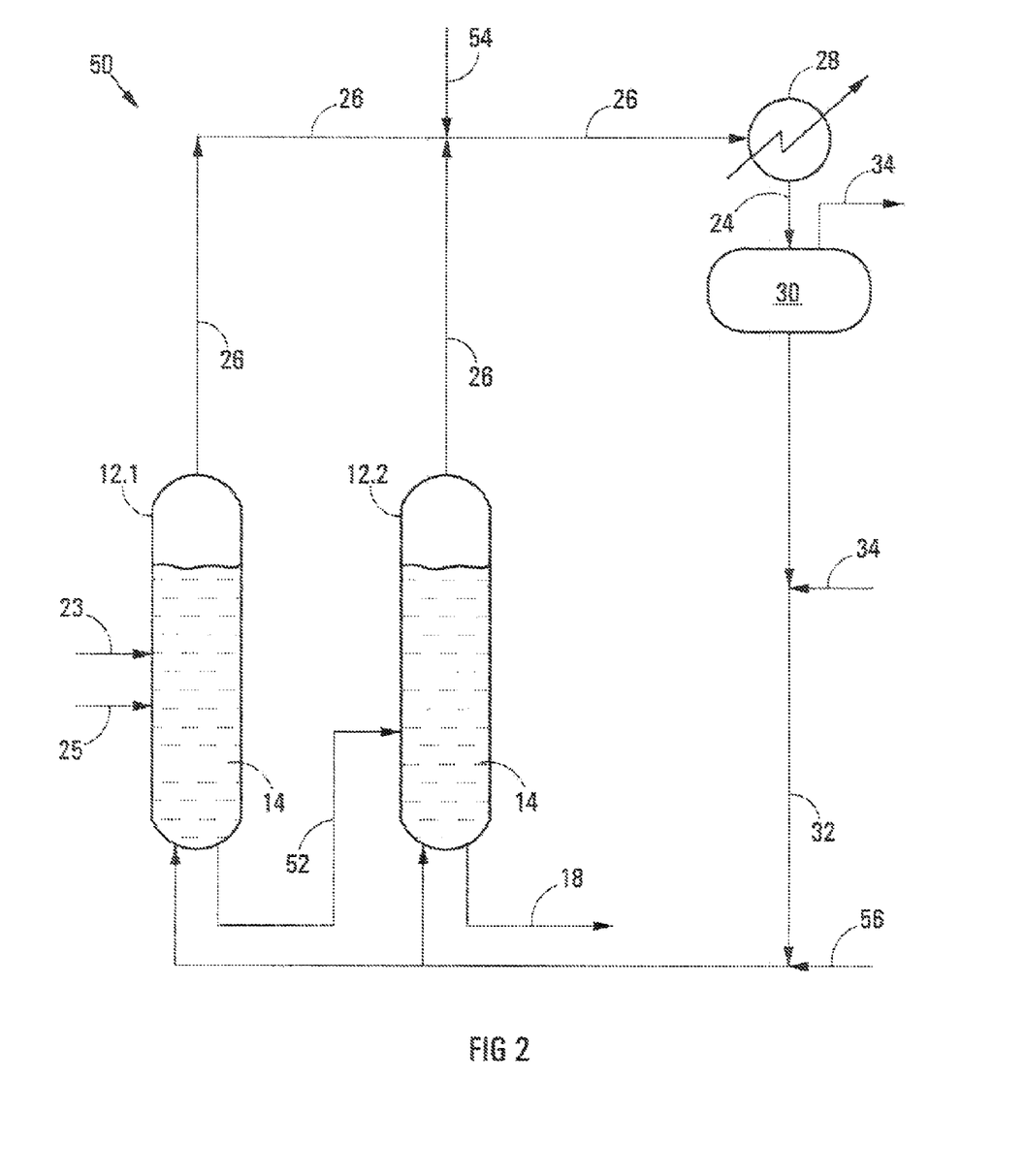
FIG. 2 shows another, more complex embodiment of a process in accordance with the invention for polymerising or oligomerising a hydrocarbon.

Referring to FIG. 2 of the drawings, a more complex embodiment of the process in accordance with the invention is generally indicated by reference numeral 50. In FIG. 2, the same reference numerals have been used as far as possible as have been used in FIG. 1 to indicate the same or similar parts or features.

The process 50 includes two reactors 12.1 and 12.2. The reactors 12.1 and 12.2 are in series as far as the bulk liquid phase 14 is concerned and a liquid phase transfer line 52 is thus provided to transfer liquid phase from the reactor 12.1 to the reactor 12.2. As far as the liquid ethylene feed is concerned, the reactors 12.1 and 12.2 are however in parallel so that the liquid ethylene feed enters both reactors 12.1 and 12.2 at their bottoms, via line 32.

Liquid phase is transferred from the reactor 12.1 to the reactor 12.2 by means of the liquid phase transfer line 52 (where the impetus for transfer is provided by a difference in pressure between reactors 12.1 and 12.2), before being withdrawn by means of the liquid phase withdrawal line 18. Recycled liquid ethylene and liquid propane and fresh ethylene feed introduced by means of the gaseous ethylene feed line 54 are however fed in parallel by means of the liquid ethylene recycle line 32 into the bottoms of the reactors 12.1 and 12.2.

Although not shown in FIG. 2, the process 50 may naturally include a treatment stage such as the treatment stage 20 to recover ethylene and propane from the liquid phase withdrawn by means of the liquid phase withdrawal line 18, as well as further treatment stages to recover and recycle solvent and to recover unreacted ethylene and uncondensed propane from the gaseous product withdrawn by means of the gaseous product line 34.

The Applicant has performed cold model experiments on a vapourising butane system to understand the effects of rapid vapourisation on bulk mixing and circulation. The butane system consisted of a water-filled 10-liter glass vessel with an inside diameter of 20 cm, into which sub-cooled liquid butane was fed through a single quarter inch tube. A colour (potassium permanganate) tracer was added to highlight flow patterns and local velocities.

When the butane was simply fed into the water, it was clear that all of the butane immediately bubbled upwards in a plume from the injector, imparting very little mixing to the liquid below that point. Zones outside of the plume of rising butane showed low flow and low turbulence. Distinct zones of high and low mixing could be discerned inside the reactor, evidenced by the absence of bubbles in the low flow regions. This has been confirmed by results of CFD simulation. These phenomena explain the behaviour of a tetramerisation piloting reactor operated by the Applicant, where excessive polymer build-up on the bottom dish is believed to be due to low turbulence under the ethylene injector entering the pilot scale reactor from the side.

When the butane injector was arranged so that injected butane impinges against a bottom dish of the glass vessel, low flow regions were eliminated and even dissipation of energy in the bulk of the water was promoted, as evidenced by a more uniform bubble size distribution throughout the liquid. The liquid bulk appeared murky, indicative of fine bubbles distributed throughout the liquid. This suggests that careful consideration must be given to the manner in which the liquid ethylene and liquid propane are fed into the bubbling column of bulk liquid phase to ensure even distribution of ethylene and propane bubbles throughout the bulk liquid phase, when the process of the invention is employed.

Figure 3:
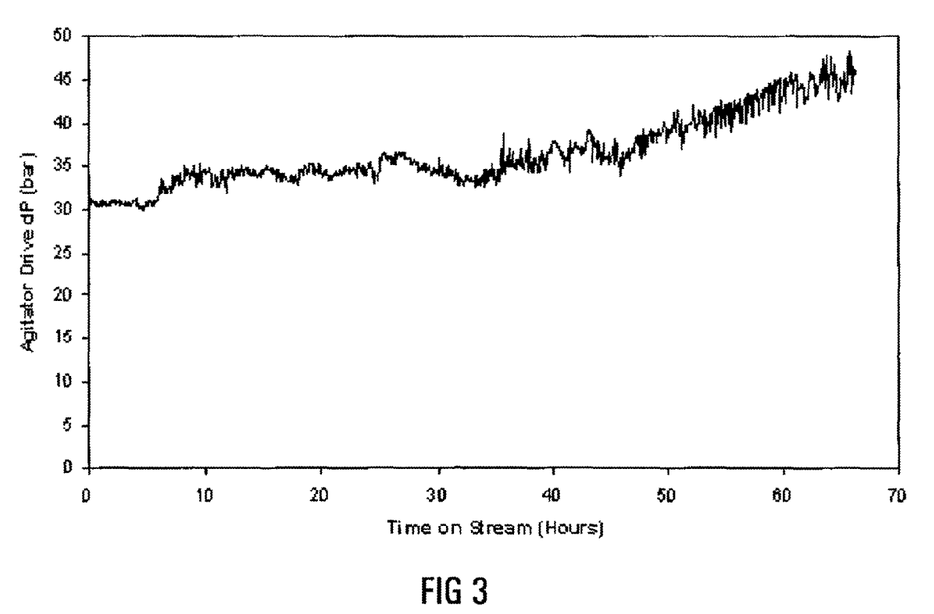
FIG. 3 shows a graph of the load on an agitator, represented by hydraulic drive pump differential pressure, in a pilot plant oligomerisation reactor subjected to fouling caused by the precipitation of polymer on the agitator.
Figure 4:
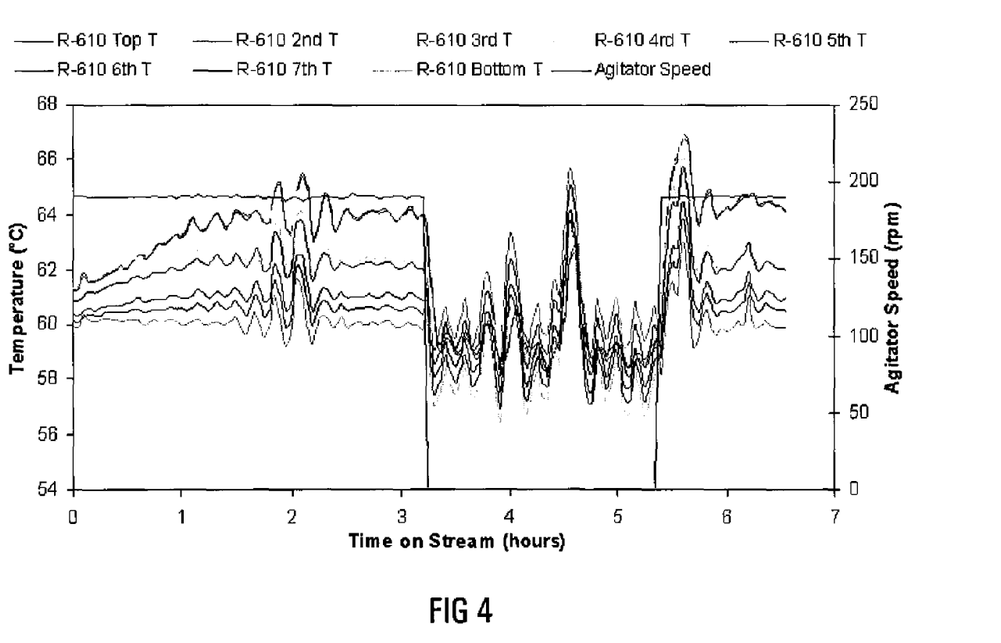
FIG. 4 shows graphs of axial pilot plant reactor temperature profile and agitator speed, for the pilot plant reactor of FIG. 3.

The Applicant believes that the process 10, 50, as illustrated, is less prone to the risk of fouling, compared to conventional processes for polymerising or oligomerising a hydrocarbon. This risk of fouling, for conventional polymerisation or oligomerisation processes, particularly those including an agitator in the reactor, is a significant problem. FIG. 3 illustrates the increased load on an agitator with time on stream under reaction conditions due to precipitation of polymer on the agitator of an oligomerisation pilot plant making use of an hydraulic drive. Liquid ethylene was used as a feed. As will be noted, the hydraulic drive pump differential pressure increases with increasing load to maintain the agitator at a target speed. This increased load is caused by fouling of the agitator. FIG. 4 shows that switching off the agitator of said pilot plant reactor is not detrimental to the axial reactor temperature profile in said reactor. Although there is a temperature oscillation when the agitator is switched off, caused by non-optimised control tuning, it will be noted that the temperature profile of each of the axially located thermocouples is consistent with the others and remains within a tight temperature tolerance.

By using a suitable evaporative cooling medium, the process 10, 50, as illustrated, allows the use of plant cooling water as cooling utility for the condensation of the bulk of the gaseous components withdrawn from the bulk liquid phase. This obviates the need for an external refrigeration unit for the partial condenser 28, which provides a significant capital and operating cost advantage for the process 10, 50, as illustrated, compared to conventional processes for polymerising or oligomerising a hydrocarbon.

The invention claimed is:

1. A process for polymerising or oligomerising a hydrocarbon, the process including:
    feeding liquid ethylene as a liquid hydrocarbon reactant and a liquid evaporative cooling medium into a bulk liquid phase which includes polymeric or oligomeric product admixed with a catalyst;
    allowing at least a portion of the liquid hydrocarbon reactant and the liquid evaporative cooling medium to vapourise as the liquid hydrocarbon reactant and the liquid evaporative cooling medium enter the bulk liquid phase to form bubbles rising through the bulk liquid phase thereby inducing turbulence and creating mixing inside the bulk liquid phase, with the hydrocarbon reactant polymerising or oligomerising to form the polymeric or oligomeric product and with the evaporation of both the liquid hydrocarbon reactant and the liquid evaporative cooling medium effecting heat removal from the bulk liquid phase;
    allowing gaseous components comprising any unreacted vapourised hydrocarbon reactant and vapourised cooling medium and any gaseous product that may have formed to disengage from the bulk liquid phase into a head space above the bulk liquid phase;
    withdrawing the gaseous components from the head space;
    cooling the gaseous components withdrawn from the head space, forming condensed hydrocarbon reactant and condensed cooling medium and gaseous product;
    separating the condensed hydrocarbon reactant and condensed cooling medium from the gaseous product and withdrawing the gaseous product;
    recycling the condensed hydrocarbon reactant and the condensed cooling medium to the bulk liquid phase; and
    withdrawing liquid phase which includes polymeric or oligomeric product from the bulk liquid phase.

2. The process as claimed in claim 1, in which the bulk liquid phase is contained in a bubbling column reactor, with the rising bubbles creating turbulence in the bulk liquid phase, thereby also mixing the bulk liquid phase.

3. The process as claimed in claim 1, in which the bulk liquid phase is at a temperature below its boiling point.

4. The process as claimed in claim 1, in which the bulk liquid phase includes an inert solvent.

5. The process as claimed in claim 1, in which heat removal from the bulk liquid phase is at least predominantly effected by means of the latent heat required for evaporation of the liquid evaporative cooling medium and the liquid hydrocarbon reactant, with sufficient liquid evaporative cooling medium and liquid hydrocarbon reactant being fed and recycled to the bulk liquid phase to balance any reaction exotherm, thereby approaching isothermal behaviour, i.e. maintaining a steady temperature in the bulk liquid phase.

6. The process as claimed in claim 1, in which the liquid hydrocarbon reactant being fed to the bulk liquid phase is sub-cooled.

7. The process as claimed in claim 1, in which the bulk liquid phase is at an operating pressure of at least 10 bar(a) and the temperature of the bulk liquid phase is between 30 and 100° C.

8. The process as claimed in claim 1, in which the evaporative cooling medium is a hydrocarbon which acts as an inert in the oligomerising or polymerising reactions, and which acts to increase the bubble point temperature of an admixture or condensate obtained by condensing the vapourised hydrocarbon reactant and the vapourised evaporative cooling medium withdrawn from the head space above the bulk liquid phase, disregarding other lighter components which may be present in the gaseous components withdrawn from the head space above the bulk liquid phase.

9. The process as claimed in claim 1, in which the evaporative cooling medium, and the concentration of the evaporative cooling medium in the bulk liquid phase, are selected such that the bubble point temperature of the gaseous components withdrawn from the head space above the bulk liquid phase, at the pressure at which the gaseous components are cooled for condensation purposes, is at least 30° C.

10. The process as claimed in claim 1, in which the evaporative cooling medium is an inert component or mixture of components that does not react with components of the bulk liquid phase, having a normal boiling point within the range of −20 to −60° C.

11. The process as claimed in claim 1, in which the evaporative cooling medium is selected from the group consisting of propane, cyclopropane, chlorodifluoromethane, difluoromethane, 1,1,1-trifluoroethane, pentafluoroethane, octafluoropropane, 1,1,1,2-tetrafluoroethane, trifluorobromomethane, chlorotrifluoroethylene, chloropentafluoroethane, ethyl-fluoride, 1,1,1-trifluoroethane, chloropentafluoroethane, and mixtures of two or more of these.

12. The process as claimed in claim 1, in which the bulk liquid phase forms part of a first oligomerisation stage and which includes feeding the withdrawn liquid phase from the first oligomerisation stage to a second oligomerisation stage comprising bulk liquid phase, and feeding said liquid hydrocarbon reactant also into the bulk liquid phase of the second oligomerisation stage, to form further polymeric or oligomeric product, the process thus using at least two oligomerisation stages in series for the bulk liquid phase, with fresh liquid hydrocarbon reactant being fed in parallel into the bulk liquid phase of each oligomerisation stage.

13. The process as claimed in claim 1, in which the evaporative cooling medium also acts as an inert solvent or diluent to limit incorporation of desirable polymeric or oligomeric product in heavier by-products, with no other solvent being added to the bulk liquid phase.

14. A process for polymerising or oligomerising a hydrocarbon, the process including
    feeding liquid ethylene as a liquid hydrocarbon reactant and a liquid evaporative cooling medium into a bulk liquid phase which includes polymeric or oligomeric product admixed with a catalyst;
    allowing at least a portion of the liquid hydrocarbon reactant and the liquid evaporative cooling medium to vapourise as the liquid hydrocarbon reactant and the liquid evaporative cooling medium enter the bulk liquid phase to form bubbles rising through the bulk liquid phase thereby inducing turbulence and creating mixing inside the bulk liquid phase, with the hydrocarbon reactant polymerising or oligomerising to form the polymeric or oligomeric product and with the evaporation of both the liquid hydrocarbon reactant and the liquid evaporative cooling medium effecting heat removal from the bulk liquid phase;

allowing gaseous components comprising any unreacted vapourised hydrocarbon reactant and vapourised cooling medium and any gaseous product that may have formed to disengage from the bulk liquid phase into a head space above the bulk liquid phase;

withdrawing the gaseous components from the head space;

cooling the gaseous components withdrawn from the head space, forming condensed hydrocarbon reactant and condensed cooling medium and uncondensed gaseous components;

separating the condensed hydrocarbon reactant and condensed cooling medium from the uncondensed gaseous components and withdrawing the uncondensed gaseous components, including ethane, thereby to reduce the partial pressure of ethane over the bulk liquid phase and to increase the partial pressure of ethylene over the bulk liquid phase;

recycling the condensed hydrocarbon reactant and the condensed cooling medium to the bulk liquid phase; and withdrawing liquid phase which includes polymeric or oligomeric product from the bulk liquid phase.

15. A process for polymerising or oligomerising a hydrocarbon, the process including feeding liquid ethylene as a liquid hydrocarbon reactant and a liquid evaporative cooling medium into a bulk liquid phase which includes polymeric or oligomeric product admixed with a catalyst;

allowing at least a portion of the liquid hydrocarbon reactant and the liquid evaporative cooling medium to vapourise as the liquid hydrocarbon reactant and the liquid evaporative cooling medium enter the bulk liquid phase to form bubbles rising through the bulk liquid phase thereby inducing turbulence and creating mixing inside the bulk liquid phase, with the hydrocarbon reactant polymerising or oligomerising to form the polymeric or oligomeric product and with the evaporation of both the liquid hydrocarbon reactant and the liquid evaporative cooling medium effecting heat removal from the bulk liquid phase;

allowing gaseous components comprising any unreacted vapourised hydrocarbon reactant and vapourised cooling medium and any gaseous product that may have formed to disengage from the bulk liquid phase into a head space above the bulk liquid phase;

withdrawing the gaseous components from the head space;

cooling the gaseous components withdrawn from the head space, forming condensed hydrocarbon reactant and condensed cooling medium and uncondensed gaseous components;

separating the condensed hydrocarbon reactant and condensed cooling medium from the uncondensed gaseous components and withdrawing the uncondensed gaseous components;

treating the uncondensed gaseous components to separate at least unreacted ethylene from the uncondensed gaseous components;

recycling the condensed hydrocarbon reactant and the condensed cooling medium to the bulk liquid phase; and withdrawing liquid phase which includes polymeric or oligomeric product from the bulk liquid phase.

\* \* \* \* \*